United States Patent [19]

Crawford

[11] Patent Number: 5,968,503
[45] Date of Patent: Oct. 19, 1999

[54] USE OF STREPTOMYCES BACTERIA TO CONTROL PLANT PATHOGENS AND DEGRADE TURF THATCH

[75] Inventor: Donald L. Crawford, Moscow, Id.

[73] Assignee: Idaho Research Foundation, Inc., Moscow, Id.

[21] Appl. No.: 08/930,031

[22] PCT Filed: Apr. 1, 1996

[86] PCT No.: PCT/US96/04501

§ 371 Date: Jan. 9, 1998

§ 102(e) Date: Jan. 9, 1998

[87] PCT Pub. No.: WO96/29874

PCT Pub. Date: Oct. 30, 1996

Related U.S. Application Data

[63] Continuation-in-part of application No. 08/415,353, Mar. 31, 1995, Pat. No. 5,527,526, which is a continuation-in-part of application No. 08/085,448, Jun. 30, 1993, Pat. No. 5,403,584.

[51] Int. Cl.⁶ .............................. A01N 63/00; C12N 1/20; D21C 1/00

[52] U.S. Cl. .................................... 424/93.43; 435/253.5; 435/277; 435/898

[58] Field of Search ........................ 424/93.43; 435/277, 435/253.5, 838

[56] References Cited

U.S. PATENT DOCUMENTS

| | | |
|---|---|---|
| 3,160,560 | 12/1964 | De Boer et al. . |
| 4,053,627 | 10/1977 | Scher . |
| 4,478,747 | 10/1984 | Crawford et al. ........................ 435/72 |
| 4,534,965 | 8/1985 | Brown et al. . |
| 4,668,512 | 5/1987 | Lewis et al. . |
| 5,403,584 | 4/1995 | Crawford et al. . |
| 5,527,526 | 6/1996 | Crawford . |

FOREIGN PATENT DOCUMENTS

| | | |
|---|---|---|
| 676 933 | 8/1966 | Belgium . |
| 2 524 486 | 10/1983 | France . |
| WO 9318135 | 9/1993 | WIPO . |
| WO A9427443 | 12/1994 | WIPO . |
| WO A9501099 | 1/1995 | WIPO . |

OTHER PUBLICATIONS

Crawford et al., Applied and Environmental Microbiology, "Isolation and Characterization of Actinomycete Antagonists of a Fungal Root Pathogen" vol. 59, No. 11, pp. 3899–3905 (1993).

Database WPI, Section Ch, Week 9416, Derwent Publications Ltd., London, GB; Class C05, AN 94–128745.

Crawford, D.L., Chemical Abstracts, "The role of actinomycetes in the decomposition of lignocellulose" Abstract No. 107:232712 (1986).

Ames, "Mycorrhiza development in onion in response to inoculation with chitin–decomposing actinomycetes," New Phytol. 112:423–427 (1989).

Bolton, "Effects of Amending Soilless Growing Mixtures With Soil Containing Antagonistic Organisms on Root Rot and Blackleg of Geranium (*Pelargonium Hortorum*) Caused by Pythium Splendens," Can. J. Plant Sci. 58:379–383 (Apr. 1978).

Bolton, "Control of *Pythium aphanidermatum* in poinsettia in a soilless culture by *Trichoderma viride* and a Streptomyces sp.," Canadian Journal of Plant Pathology 2:93–95 (1980).

Broadbent et al., "Bacteria and Actinomycetes Antagonistic to Fungal Root Pathogens in Australian Soils," Aust. J. biol. Sci. 24:925–44 (1971).

Chambers and Millington, "Studies on Fusarium Species Associated with a Field Planting of 'Pathogen–tested' Potatoes," Aust. J. Agric. Res. 25:293–7 (1974).

Chibata and Tosa, "Use of Immobilized Cells," Ann. Rev. Biophys. Bioeng. 10:197–216 (1981).

DeFrank and Putnam, "Screening Procedures to Identify Soil–Borne Actinomycetes That Can Produce Herbicidal Compounds," Weed Science 33:271–274 (1985).

Filonow and Lockwood, "Evaluation of Several Actinomycetes and the Fungus *Hyphochytrium catenoides* of Biocontrol Agents for Phytophthora Root Rot of Soybean," Plant Disease, vol. 69, No. 12, pp. 1033–1036 (1985).

Fravel et al., "Encapsulation of Potential Biocontrol Agents in an Alginate–Clay Matrix," Phytopathology, vol. 75, No. 7, pp. 774–777 (1985).

Hussain et al., "Biological Control of *Macrophomina phaseolina* Charcoal Rot of Sunflower and Mung Bean," J. Phytopathology 130:157–160 (1990).

Lahdenpera et al., "Mycostop—A Novel Biofungicide Based on Streptomyces Bacteria," published prior to 1991.

Liljeroth et al., "Assimilate Translocation to the Rhizosphere of Two Wheat Lines and Subsequent Utilization by Rhizosphere Microorganisms at Two Soil Nitrogen Concentrations," Soil Biol. Biochem., vol. 22, No. 8, pp. 1015–1021 (1990).

(List continued on next page.)

*Primary Examiner*—Sandra E. Saucier
*Assistant Examiner*—Afremova Vera
*Attorney, Agent, or Firm*—Klarquist Sparkman Campbell Leigh & Whinston, LLP

[57] ABSTRACT

This invention relates to biocontrol formulations suitable for reducing the susceptibility of plants to fungal phytopathogens and for degrading turf thatch. In one aspect of the invention, a culture of strain Streptomyces sp. WYE 53 ATCC 55750 is incorporated into suitable delivery medium and applied to plant seeds and roots. Another aspect of the invention is directed to a composition comprising cultures of strains Streptomyces sp. WYE 53 ATCC 55750 and/or Streptomyces sp. YCED 9 ATCC 55660 and to a method for degrading turf thatch by contacting the turf thach with cultures of strains Streptomyces sp. WYE 53 ATCC 55750 and/or Streptomyces sp. YCED 9 ATCC 55660 which are incorporated into suitable delivery medium.

8 Claims, No Drawings

OTHER PUBLICATIONS

Lingappa and Lockwood, "Chitin Media for Selective Isolation and Culture of Actinomycetes," Phytopathology 52:317–323 (1962).

Lynch et al., "Prospects for control of Pythium damping–off of lettuce with Trichoderma, Gliocladium, and Enterobacter spp.," Biol Fertil Soils 11:1–5 (1991).

M. L. Lahdenperä, "The Control of Fusarium Wilt on Carnation with a Streptomyces Preparation," Acta Horticulturae 216:85–92 (1987).

Merriman et al., "Effect of Bacillus and Streptomyces spp. Applied to Seed," in E. Bruehl (ed.), Biology & Control of Soil–Borne Plant Pathogens, pp. 130–133 (1977).

Meyer and Linderman, "Selective Influence on Populations of Rhizosphere or Rhizoplane Bacteria and Actinomycetes by Mycorrhizas Formed by *Glomus Fasciculatum*," Soil Biol. Biochem. vol. 18, No. 2, pp. 191–196 (1986).

Miller et al., "Variation and composition of bacterial populations in the rhizospheres of maize, wheat, and grass cultivars," Can. J. Microbiol. 35:656–660 (1989).

Miller et al., "Fluctuations in the fluorescent pseudomonad and actinomycete populations of rhizosphere and rhizoplane during the growth of spring wheat," Can. J. Microbiol. 36:254–258 (1990).

Miller et al., "The Dynamics of Actinomycetes and Fluorescent Pseudomonads in Wheat Rhizoplane and Rhizosphere," Symbiosis 9:389–391 (1990).

Mohamed, "Physiological and Antagonistic Activities of Streptomycetes in Rhizosphere of Some Plants," Egypt. J. Phytopathol. 14:121–128 (1982).

Panosyan et al., "The Nature of Physiologically Active Substances of Actinomycetes and the Effect of Their Metabolites on Plant Growth," Plant Microbe Relationships, pp. 241–245 (1965).

Reddi and Rao, "Antagonism of Soil Actinomycetes to Some Soil–Borne Plant Pathogenic Fungi," Indian Phytopathology, vol. 24, pp. 649–57 (1971).

Rothrock and Gottlieb, "Role of antibiosis in antagonism of *Streptomyces hygroscopicus* var. *geldanus* to *Rhizoctonia solani* in soil," Can. J. Microbiol. 30:1440–1447 (1984).

Sabaou and Bounaga, "Actinomycetes parasites de champignons: etude des especes, specificite de l'action parasitaire au genre Fusarium et antagonisme dans le sol envers *Fusarium oxysporum* f.sp. *albedinis* (Killian et Maire) Gordon," Can. J. Microbiol. 33:445–451 (1987).

Scrinivasan et al., "Physiology and nutritional aspects of actinomycetes: an overview," World Journal of Microbiology and Biotechnology 7:171–184 (1991).

Singh and Mehrotra, "Biological Control of *Rhizoctonia Bataticola* on Gram by Coating Seed with Bacillus and Streptomyces spp. and their Influence on Plant Growth," Plant and Soil 56:475–483 (1980).

Stevenson, "Antibiotic Activity of Actinomycetes in Soil as Demonstrated by Direct Observation Techniques," J. gen. Microbiol. 15:372–380 (1956).

Suh et al., "Production of antifungal metabolites by Streptomyces WYEC 108," Abstract, Society for Industrial Microbiology 49th Annual Meeting (Jul. 1992).

Sutherland and Papavizas, "Evaluation of Oospore Hyperparasites for the Control of Phytophthora Crown Rot of Pepper," J. Phytopathology 131:33–39 (1991).

Tahvonen, "Mycostop—ett biologiskt bekampningsmedel motsvampsjukdomar" ("Mycostop, biological formulation for control of fungal diseases"), *Växtskyddsnotiser* 49:5, 86–90 (1985).

Tahvonen, "Preliminary experiments into the use of Streptomyces spp. isolated from peat in the biological control of soil and seed–borne diseases in peat culture," Journal of the Scientific Agricultural Society of Finland 54:357–369 (1982).

Tahvonen and Avikainen, "The biological control of seed––borne *Alternaria brassicicola* of cruciferous plants with a powdery preparation of Streptomyces sp.," Journal of Agricultural Science in Finland 59:199–207 (1987).

Tu, "Hyperparasitism of *Streptomyces albus* on a Destructive Mycoparasite *Nectria inventa*," J. Phytopathology 117:71–76 (1986).

Turhan, "A new race of *Streptomyces ochraceiscleroticus* in the biological control of some soil–borne plant pathogens," Journal of Plant Diseases and Protection 88(7):422–434 (1981).

Turhan and Turhan, "Suppression of Damping–off on Pepper Caused by *Pythium ultimum* Trow and *Rhizoctonia solani* Kühn by Some New Antagonists in Comparison with *Trichoderma harzianum* Rifai," J. Phytopathology 126:175–182 (1989).

Walker and Connick, Jr., "Sodium Alginate for Production and Formulation of Mycoherbicides," Weed Science 31:333–338 (1983).

Williams, "Are antibiotics produced in soil?," Pedobiologia 23:427–435 (1982).

Antai et al., "Degradation of softwood, hardwood and grass lignocellulose by two Streptomyces strains", Applied and Environmental Microbiology, Aug. 1981, vol. 42, No. 2, pp. 378–380.

USE OF STREPTOMYCES BACTERIA TO CONTROL PLANT PATHOGENS AND DEGRADE TURF THATCH

This application is 371 of PCT/US96/04501 filed Apr. 1, 1996 which is a continuation-in-part of U.S. application Ser. No. 08/415,353, filed Mar. 31, 1995 (U.S. Pat. No. 5,527,526) which is a continuation-in-part of U.S. application Ser. No. 08/85,448, filed Jun. 30, 1993, (U.S. Pat. No. 5,403,584).

FIELD OF THE INVENTION

The present invention relates to new strains of Streptomyces bacteria that are capable of inhibiting the growth of soil borne plant pathogens and enhancing plant growth while also degrading turf thatch.

BACKGROUND OF THE INVENTION

Fungal phytopathogens are a cause of severe economic losses in the agricultural and horticultural industries. Many different types of fungal phytopathogens have been described: these pathogens cause plant diseases such as damping-off, white-rot, brown-rot and root-rot. Such diseases can kill emerging seedlings, reduce plant vigor and adversely affect crop yields.

To minimize fungal infections, bedding-plant nurseries may grow seedlings in steam sterilized or chemically treated soils. However, such treatments also remove beneficial microorganisms from the soil, including microorganisms that would normally compete with soil fungi. In such cases, if a fungal pathogen is accidentally introduced, it may spread rapidly and produce widespread disease.

In agricultural settings, soils infested with phytopathogenic fungi may be unsuitable for growing certain crops. For example, soybean production in Michigan and in other soybean growing states is often severely limited by Phytophthora root rot caused by the fungus *Phytophera megasperma* (Filinow and Lockwood, 1985). Species of Pythium fungi are widespread in soils in parts of California, Washington State and Idaho. *Pythium ultimum* is the most common pathogenic species encountered and is associated with pre- and post-emergence damping-off of seedlings. This species is a serious pathogen of wheat, peas and chickpeas and other crop plants grown in these soils and in soils in other states and other countries (Trapero-Casas et al., 1990; Stanghellini and Hancock, 1970; Kraft and Burke, 1971; Westerlund et al., 1988). The use of chemical agents to control fungal phytopathogens is often not practical due to high costs, lack of efficacy and the emergence of resistant strains of the fungi. Additionally, the use of chemical fungicides is not desirable from an environmental viewpoint.

It is an object of the present invention to provide new biological control means of reducing fungal pathogen infection of plants. It is also an object of this invention to simultaneously provide new means for the biological degradation of turf thatch.

SUMMARY OF THE INVENTION

The foregoing object has been achieved by the isolation of a number of actinomycete bacteria that are shown to be effective in both inhibiting the growth of fungal phytopathogens and in degrading turf thatch. In particular, three of the isolated actinomycete bacteria, herein named Streptomyces WYEC 108, Streptomyces WYE 53 and Streptomyces YCED 9, are shown to exhibit strong antagonism towards a wide range of fungal plant pathogens, including pathogens that cause the plant diseases commonly known as damping-off, root rot, white rot and brown rot. Biologically pure cultures of Streptomyces YCED 9 and Streptomyces WYE 53 are one aspect of the present invention.

Streptomyces YCED 9 and Streptomyces WYE 53 are also shown to be effective in degrading turf thatch, the dead and dying grassy stem material that accumulates in turf. As a result of their ability to metabolize thatch as a carbon source, YCED 9 and WYE 53 are well suited to growth and persistence in the rhizosphere of plants. Such growth also allows optimal biocontrol activity.

The present invention sets forth various compositions suitable for treating plant seeds or plant roots with Streptomyces YCED 9 or WYE 53. Such compositions are useful to reduce the susceptibility of plants to fungal infection, to prevent fungal infection and to reduce the accumulation of turf thatch.

In one embodiment, such compositions comprise a biologically pure culture of Streptomyces YCED 9 or a biologically pure culture of Streptomyces WYE 53 and a delivery medium. The combination of Streptomyces WYE 53 and YCED 9 is shown to produce a superior thatch-degrading ability than the individual strains under certain conditions. Thus, another embodiment of the invention is a composition produced by combining a biologically pure culture of WYE 53 and a biologically pure culture of YCED 9. This YCED 9/WYE 53 composition may also be combined with a delivery medium.

The delivery medium serves as a support medium for the Streptomyces bacteria; it preserves the viability of the bacteria during storage and, depending on its formulation, can provide nutrients to both the Streptomyces bacteria and plants to which it is applied. Many substrates are suitable as a delivery medium. In particular embodiments, the delivery medium may comprise alginate gel, peat moss, sand, cornmeal or other organic or inorganic media. In certain embodiments, a nitrogen source may be incorporated into the delivery medium. In one embodiment, the present invention encompasses a delivery medium which comprises peat moss, sand and cornmeal together with Streptomyces YCED 9 or WYE 53 or a combination of YCED 9 and WYE 53, In a preferred embodiment, the delivery medium comprises at least $10^5$ colony forming units of the Streptomyces bacteria per gram of delivery medium. In a more preferred embodiment, the delivery medium comprises at least $10^8$ colony forming units of the Streptomyces spores per gram of delivery medium.

In another preferred formulation, the delivery medium comprises peat moss and sand and spores of the Streptomyces bacteria at $10^8$–$10^9$ colony forming units per gram.

In another embodiment, the compositions comprising a biologically pure culture of Streptomyces YCED 9 or Streptomyces WYE 53, or a combination of YCED 9 and WYE 53, and a delivery medium may be combined with supplements to enhance plant growth, such as fertilizers or other forms of plant nutrients. Other supplements to further reduce pest or disease damage may also be utilized; these include chemical pesticides and other biological control agents that are compatible with the Streptomyces strains. In one embodiment, the composition includes a biologically pure culture of Streptomyces YCED 9, a delivery medium and another biological control agent, such as another microorganism that has the ability to inhibit fungal growth.

In another embodiment, the present invention encompasses alginate gel pellets containing Streptomyces YCED 9 or Streptomyces WYE 53 or a combination of these bacteria. Such pellets can be added directly to the roots of growing plants or to horticultural or agricultural soils to reduce damage to plants caused by phytopathogenic fungi.

The present invention also encompasses methods for reducing the susceptibility of a plant to fungal infection. In one embodiment, this method comprises delivering Streptomyces YCED 9 or Streptomyces WYE 53 or a combination of these bacteria to the roots of a plant. In another embodiment, the method comprises immersing seeds in a composition that contains Streptomyces YCED 9 or Streptomyces WYE 53 or a combination of these bacteria and thereafter planting the coated seeds in a suitable growth medium. A suitable composition for use in this method is an alginate gel containing the Streptomyces bacteria. An alternative composition for use in this method is a methyl cellulose solution containing the Streptomyces bacteria.

Finally, the present invention also encompasses methods for degrading turf thatch. In one embodiment, this method comprising contacting the turf thatch with a composition comprising a biologically pure culture of Streptomyces YCED 9, or a biologically pure culture of Streptomyces WYE 53, or a culture produced by combining Streptomyces YCED 9 with Streptomyces WYE 53.

DETAILED DESCRIPTION OF THE INVENTION

The present invention pertains to the isolation of a number of actinomycete strains from soils. A number of these strains are shown to be effective in reducing the effects of fungal pathogens on plants, including (but not limited to) lettuce, chickpea and pepper. In particular, the present invention pertains to two Streptomyces strains herein referred to as Streptomyces WYE 53 and Streptomyces YCED 9. These Streptomyces strains are shown to exhibit strong antagonism towards a wide range of fungal phytopathogens, including pathogens that cause pre- and post-emergence damping off of seedlings, root rot, brown rot and white rot. As such, these Streptomyces strains are particularly suitable as biocontrol agents that can be used to protect plants against infection by these phytopathogens. Thus, Streptomyces strains WYE 53 and YCED 9 are useful in methods for reducing the susceptibility of plants to fungal infection; plants treated with these microorganisms will show reduced effects of fungal infection.

Fungal infection of susceptible untreated plants affects certain growth characteristics of such plants. For instance, untreated plants exposed to fungal pathogens may show significant reductions in plant height, plant biomass and crop yield compared to plants not exposed to the fungal pathogen. In preferred embodiments of the present of the invention, the ability of WYE 53 and YCED 9 to reduce the susceptibility of plants to fungal infection means that plants treated with these bacteria and subsequently exposed to the fungal pathogen will show less severe reductions in plant height, plant biomass and crop yield than untreated plants exposed to the fungal pathogen.

In more preferred embodiments, plants treated with the Streptomyces strains of the present invention and exposed to the fungal pathogen will show growth characteristics similar to the untreated, unexposed plants. In most preferred embodiments, plants treated with these strains and exposed to the fungal pathogen will show growth characteristics superior to the untreated, unexposed plants.

The Streptomyces strains of the present invention are potent antifungal biocontrol agents. These strains effectively inhibit the growth of a wide range of fungal pathogens and colonize the roots of plants in the presence of competition from rhizosphere microflora. Strain YCED 9 produces fungal cell wall lytic enzymes and antifungal metabolites, including multiple antibiotics. Strain YCED 9 is also a mycoparasite of fungal hyphae and spores, and maintains a quantitatively significant presence in the rhizosphere for months.

Strains YCED 9 and WYE 53 are also shown to have the ability to colonize and then degrade turf thatch. Turf thatch is the lignocellulosic material comprising dead grass stems and other vegetative matter that accumulates in turf. The ability of YCED 9 and WYE 53 to degrade this material enhances the ability of these bacteria to persist in the rhizosphere, where they act to control the growth of fungal pathogens. YCED 9 and WYE 53 may therefore be applied to turf, such as lawns or golf courses, for the dual purposes of degrading turf thatch and preventing the growth of fungal turf pathogens. Further, these two strains are shown to have a synergistic effect when applied to turf thatch together. Thus, another aspect of the invention is the use of a mixture of YCED 9 and WYE 53 to degrade turf thatch.

Also encompassed by this invention are means of producing vegetative cells or spores of the Streptomyces strains for incorporation into a delivery medium. The composition comprising the vegetative cells and spores of these bacteria and the delivery medium has a long shelf life and is suitable for delivering the bacteria to plants for effective control of fungal phytopathogens.

Materials and Methods
Bacterial Growth Media

All bacterial growth media were prepared using distilled water and sterilized by autoclaving prior to use. All bacterial samples were handled using standard aseptic laboratory techniques to maintain purity.

YGM (yeast extract/glucose/mineral salts) medium: 0.6% (wt/vol) yeast extract (Difco Laboratories, Detroit, Mich.), 1.0% (wt/vol) glucose, and phosphate mineral salt solution (5.3 g of $Na_2HPO_4$, 1.98 g of $KH_2PO_4$, 0.2 g of $MgSO_4.7H_2O$, 0.2 g of NaCl, 0.05 g $CaCl_2.2H_2O$, plus 1.0 ml of trace elements (Pridham and Gottlieb, 1948) per liter of deionized $H_2O$; pH 7.1 to 7.2). The solution of trace elements consisted of 0.64 g of $CuSO_4.5H_2O$, 0.11 g of $FeSO_4.7H_2O$, 0.79 g of $MnCl_2.4H_2O$, 0.15 g of $ZnSO_4.7H_2O$ in 100 ml of distilled water.

WYE (water/yeast extract/agar) medium, modified from Reddi and Rao (1971): yeast extract (Oxoid, 0.25 g/l) as the sole carbon and nitrogen source, and agar (Oxoid, 18.0 g/l). The medium was buffered to pH 7.2–7.4 with $K_2HPO_4$ (0.5 g/l).

WYEC (water/yeast extract/cellulose/agar): WYE agar to which a thin overlay agar was added. The overlay agar contained 0.25 g/l of cellulose (Solka Floc, Sigma Chemical Co.) and 18.0 g/l agar in distilled water.

CYD (cassamino acids/yeast extract/dextrose agar) medium: casamino acids (Difco: 0.5 g/l), yeast extract (Oxoid or Difco: 0.8 g/l), D-glucose (0.4 g/l), $K_2HPO_4$ (2.0 g/l; pH 7.2–7.4), and 18.0 g/l agar in distilled water.

YCED (casamino acids/yeast extract/dextrose/agar; modified from Reddi and Rao (1971)): yeast extract (Oxoid, 0.3 g/l), casamino acids (Difco, 0.3 g/l), D-glucose (0.3 g/l), and agar (Oxoid, 18.0 g/l). The medium was buffered with $K_2HPO_4$ (2.0 g/l).

CYPC (cellulose/yeast extract/peptone/compost extract/agar): cellulose (Solka Flock, Sigma Chemical Col; 5.0 g/l), yeast extract (1.0 g/l), peptone (Oxoid, 1.0 g/l), phosphate buffer (K$_2$HPO$_4$, 0.75 g/l), agar (18.0 g/l), and compost extract (100 ml/l) replacing 100 ml of distilled water in the medium. It was poured directly and not used as an overlay agar.

MSSC (mineral salts/starch/casein/agar; Turban, 1981): a mineral salts solution consisting of NaCl (2.0 g/l), MgSO$_4$17H$_2$O (0.05 g/l), CaCO$_3$ (0.02 g/l), FeSO$_4$18H$_2$O (0.01 g/l), and KNO$_3$ (2.0 g/l), plus organic constituents including soluble starch (10.0 g/l) and casein (0.3 g/l), plus agar (18.0 g/l). The medium is buffered with K$_2$HPO$_4$ (2.0 g/l).

Sporulation agar (ATCC Medium #5): yeast extract (1.0 g/l), beef extract (1.0 g/l), tryptose (2.0 g/l), FeSO$_4$ (0.01 g/l), glucose (10.0 g/l), and agar (15.0 g/l). The medium was adjusted to pH 7.2 prior to autoclaving. (17th Edition ATCC Catalogue of Bacteria and Bacteriophages). Sporulation broth is made in the same manner except the agar is omitted.

CYG medium: Casamino acids (acid hydrolysate) (5.0 g/l), yeast extract (5.0 g/l) and glucose (10.0 g/l) in distilled water, adjusted to pH 7.1–7.2.

PDA (Potato Dextrose Agar): Potato infusion (200 g/l), dextrose (20 g/l) and agar (15 g/l). This medium is available commercially from Difco Co., Detroit, Mich. Potato Dextrose Medium (PDM) is made in the same manner except that agar is omitted.

The delivery medium, comprising sand/cornmeal/water, peat moss/sand/cornmeal or sand/peat moss in ratios as set forth below, was sterilized by steam sterilization prior to use. Sterilization was typically performed by autoclaving 3 times, each time by 90 minutes. This sterilization procedure may also be used for other delivery media.

Harvesting of Bacterial Growth

For mycelial growth of Streptomyces bacteria, one liter Erlenmeyer flasks containing 500 ml YGM medium (pH 7.1–7.2) are inoculated with 20 ml of stock culture (prepared as described in Examples II and III) and incubated with shaking at 250 rpm at 30° C. for three days. Mycelia are harvested by centrifugation at 5,000 rpm for 10 minutes. Alternatively, mycelia are harvested by permitting the culture to stand until mycelia and spores settle to the bottom of the Erlenmeyer flask. Supernatant media is then decanted off and the concentrated suspension of mycelia and spores is used directly to inoculate delivery medium.

Cells and spores of Streptomyces bacteria may also be produced by growth on solid medium (for example sporulation agar or PDA). Mycelia and spores are harvested from sporulation agar or PDA by scraping the surface of the agar into distilled water or directly into the delivery medium. The suspension of spores and mycelia in water is mixed directly into the delivery medium.

For the production of spores of Streptomyces WYEC 108 two liter Erlenmeyer flasks containing 1,200 ml YGM medium were each inoculated with 50 ml of stock culture and incubated with shaking at 250 rpm at 30° C. for 12–18 days. Spores were harvested by centrifugation at 9,000 rpm for 10 minutes. Spores of Streptomyces YCED 9 and WYE 53 may be similarly produced, except that Potato Dextrose medium or sporulation medium are preferred to YGM.

Fungal Pathogens

*Pythium ultimum* PuMXL was obtained from the culture collection of the Department of Microbiology and Crop Protection at Horticulture Research International, Worthing Road, Little Hampton, West Sussex BN17 6LP, United Kingdom. White-rot fungi *Phanerochaete chrysosporium* and *Coriolus versicolor;* brown-rot fungi *Postia placenta, Caldariomyces fumago,* and *Gloeophyllum trabeum;* soil born fungal pathogens *Rhizoctonia solani, Fusarium sambucinctum, Geotrichum candidum,* and *Verticillium dahliae* came from the culture collection of professor Don L. Crawford, Department of Microbiology, Molecular Biology, and Biochemistry, University of Idaho, Moscow, Id. *Pythium irregulare, Phytophthora capsici, Phytophthora cinnamomi, Phytophthora parasitica, Sclerotinia cepivorum,* and *Sclerotinia sclerotiorum* came from the culture collection of Dr. Wesley Chun, Department of Plant Soil Entomology Science, University of Idaho, Moscow, Id. *Fusarium oxysporum* came from the culture collection of Dr. Arthur D. Partridge, Department of Forest Resources, University of Idaho, Moscow, Id. All cultures were maintained on potato dextrose agar or corn meal agar and grown at 25° C. These strains were identified as "pathogens" when obtained, but were not retested for their pathogenicity.

Bioassay Soil

For use in bioassays, soil naturally infested with *Pythium ultimum* was collected from several sites in the Palouse region near Moscow, Id. This soil was collected from the top 15 cm from fields that had been cropped with wheat and pea in the previous two seasons. The soil population of Pythium species was determined as follows: A soil dilution of 1.0 g air-dried soil in 50 ml sterilized distilled-water was thoroughly mixed with a Vortex tube mixer. A 0.1 ml sample of the well mixed dilution was placed as small droplets on 3-day-old 2% water agar plates (Stanghellini and Hancock, 1970). Plates were incubated at 25° C. and read periodically using a low power (×10) dissecting microscope with fluorescent illumination to determine the identity and numbers of Pythium species present. Colonies on each plate were checked after 12, 48 and 72 hours of incubation, before the final population was estimated. Identification was based upon the morphological characteristics of fungal mycelium of Pythium species under microscope and the growth pattern on 2% (w/v) water agar plates. Fungal colonies of a pure culture growing on 2% (w/v) water agar served as a control for visual identification purposes (Stanghellini and Hancock, 1970; Stasz et al., 1980).

Examination of this soil indicated that the population densities of *P. ultimum* and *P. irregulare* were 354±15 and 194±11 cfu/g of air-dried soil at the time of seeding (Spring, 1992), respectively. Population density of other Pythium species was 57±9 cfu/g of air-dried soil. *P. ultimum* and *P. irregulare* were the most prevalent species isolated from the collected soil.

EXAMPLE I

Isolation of Actinomycete Strains Exhibiting Antagonism Towards Fungal Phytopathogens Actinomycete strains were isolated from four rhizosphere-associated soil samples and four non-rhizosphere-associated soil samples. The isolates were isolated by serial-dilution/spread-plate techniques: dilutions of from $10^{-5}$ to $10^{-7}$ were placed onto various agar isolation media. The composition of these media is set forth in "Materials and Methods" above. Actinomycete isolates were designated according to the isolation medium on which they were isolated. These strains were then tested for utility as inhibitors of the fungal pathogen (*P. ultimum*).

To test the ability of these isolates to inhibit the growth of *P. ultimum,* an in vitro plate assay was used. Each actinomycete was streak-inoculated on corn meal agar (CMA) plates, to one side of center. The culture was incubated at 25° C. for about 8 days or until the culture had sporulated. A CMA agar block (0.5 cm$^2$) containing actively growing *P. ultimum* mycelium was then aseptically placed in the center of the plate. Incubation was continued for 96 h. After 48 and 96 h the plate was examined for inhibition in the growth of *P. ultimum*. Inhibition was indicated when *P. ultimum* mycelial growth in the direction of the actinomycete colony was retarded or prevented.

Strains that showed the ability to strongly inhibit the growth of *P. ultimum* in this in vitro antagonism assay were then assessed for their ability to degrade turf thatch. The ability to degrade turf thatch was determined by sterilizing a measured 1 g of turf thatch by autoclaving for 90 minutes on 3 consecutive days. The sterile flask was then inoculated with spores of the selected Streptomyces strain in a sterile solution of phosphate buffered yeast extract (0.3% w/v, pH 6.5–7.5). Following inoculation, the flask was incubated at 30° C. and replicate flasks were harvested periodically and the amount of thatch remaining quantified gravimetrically.

Based on these assays, two of the Streptomyces isolates, Streptomyces WYE 53 and Streptomyces YCED 9 were selected for their superior abilities both to inhibit fungal phytopathogens and to degrade turf thatch. A third strain, herein named Streptomyces WYEC 108, was selected for its ability to similarly inhibit fungal phytopathogens.

EXAMPLE II

Isolation of Streptomyces WYE 53

Strain WYE 53 was identified as a Streptomyces species on the basis of the morphological characteristics of the genus Streptomyces, as defined by Bergey's Manual of Systematic Bacteriology (1986). Following the isolation of the strain on WYE agar, colonies were restreaked onto WYE agar for purification and then transferred to agar slants, incubated at 25° C. until sporulated, and stored at 4° C. until used.

Identity of Streptomyces WYE 53

Various biochemical and physiological characteristics of strain WYE 53 were determined. Based on these characteristics, Streptomyces WYE 53 may belong to the species *Streptomyces violaceusniger* (also known as *Streptomyces hygroscopicus*) or a related species, as defined by Bergey's Manual of Determinative Bacteriology (1986).

ATCC Accession Number

A deposit of *Streptomyces WYE 53* was made under the terms of the Budapest Treaty with the American Type Culture Collection (ATCC), 10801 University Boulevard, Manassas, Va. 2011002209 on Apr. 1, 1996. This strain has been designated ATCC Accession No. 55750.

EXAMPLE III

Isolation of Streptomyces YCED 9

Strain YCED 9 was identified as a Streptomyces species on the basis of the morphological characteristics of the genus Streptomyces, as defined by Bergey's Manual of Systematic Bacteriology (1986). YCED 9 is a filamentous bacterium that produces spiral chains of spores in an aerial mycelium. As the aerial mycelium forms, the surface of colonies on agar medium turns white. Then, as the spore chains form and mature, the aerial mycelium turns from white to gray and then to black.

Following the isolation of Streptomyces YCED 9 from soil samples on YCED agar, the colonies were picked and streaked onto fresh YCED agar plates for purification. Pure colonies of YCED 9 were then transferred to PDA slants, incubated at 25° C. until sporulated, and stored at 4° C. until used. PDA is preferred for YCED 9 because the bacterium grows more rapidly and sporulates better on this medium.

Identity of Streptomyces YCED 9

Various biochemical and physiological characteristics of strain YCED 9 were determined. Based on these characteristics, Streptomyces YCED 9 may belong to the species *Streptomyces violaceusniger* (also known as *Streptomyces hygroscopicus*) or a related species, as defined by Bergey's Manual of Determinative Bacteriology (Volume 4, pages 2468–2492, 1989).

By way of comparison of Streptomyces YCED 9 to the type strain of *Streptomyces violaceusniger* (ATCC 27477), the carbohydrate utilization patterns of the two strains were determined as described in Bergey's Manual of Determinative Bacteriology (Volume 4, pages 2468–2492, 1989). In these tests, a basal agar containing inorganic mineral salts was prepared. Filter sterilized substrates (sugars, sugar alcohols, organic acids) were added to give a final concentration of 1% (w/v) concentrations, except for the organic acids, which were at 0.1% (w/v). The results, which also include tests of two organic acids are presented in Table IV below.

TABLE IV

| Carbohydrate Tested | Growth of Strain YCED 9 | Growth of S. hygroscopicus |
|---|---|---|
| Basal Medium | + (Sporulation +) | + (Sporulation +) |
| Glucose | ++++ (Sporulation +) | ++++ (Sporulation +) |
| Sucrose | + (Sporulation +) | + (Sporulation +) |
| Galactose | +++ (Sporulation +) | ++++ (Sporulation +) |
| Inositol | ++ (Sporulation +) | + (Sporulation +) |
| Xylose | +++ (Sporulation +) | ++ (Sporulation +) |
| Fructose | +++ (Sporulation +) | +++ (Sporulation +) |
| Xylitol | ++ (Sporulation +) | ++ (Sporulation +) |
| Arabinose | + (Sporulation −) | +++ (Sporulation −) |
| Rharunose | ++++ (Sporulation −) | ++ (Sporulation +) |
| Lactose | +++ (Sporulation −) | ++ (Sporulation +) |
| Na Pyruvate | ++ (Sporulation +) | ++ (Sporulation +) |
| Na acetate | + (Sporulation +) | + (Sporulation +) |

(±) means little if any growth, while (++++) means copious growth. Intermediate levels of growth are recorded at +, ++, and +++. Basal medium value represents growth with no added carbon source.

Cultures of Streptomyces YCED 9 excrete multiple metabolites that are inhibitory to root pathogenic fungi and other microorganisms. These metabolites are produced maximally in liquid media after the culture has entered stationary phase. In flask cultures in a typical medium such as CYD broth at pH 7.0, maximal activity, as shown with biolyses or fungal inhibition on agar plates, is found after 16 days at 30° C., although significant activity is observed after 8–10 days. In contrast, cellular growth peaks after 2–3 days.

The excreted antimicrobial metabolites of Streptomyces YCED 9 are only partially inactivated by boiling and are resistant to freeze drying. The metabolites are not inactivated by protease, suggesting that they are not enzymes. Lyophilized culture supernatants containing the antimicrobial metabolites can be redissolved in water (for example at 6% w/v) but such solutions are not stable for more than a few days. However, when redissolved in ethanol at 6% w/v, the antimicrobial activity is stable at room temperature for at least 20 days.

The antimicrobial compounds produced by Streptomyces YCED 9 are extractable with organic solvents. These compounds are soluble in methanol, ethanol, n-propanol, isopropanol, and are slightly soluble in n-butanol, isobutanol, and isoamyl alcohol. Enhanced stability is observed at more basic pH levels (pH7–11) compared to acidic pH levels (<pH4). The antimicrobial compounds exhibit medium polarity on thin layer chromatography silica gel plates. The behavior of the compounds on thin layer chromatography plates using pyridine/water excludes the possibility of the compounds being primarily members of the hygromycin family. Thin layer chromatography using a methanol/chloroform solvent system shows the presence of three antimicrobial compounds. One of these compounds is associated with a strong anti-fungal activity while the other two exhibit a strong anti-bacterial activity against a Bacillus. The mobility of these compounds on thin layer chromatography suggests that they are members of the macrolide group of antibiotics and are not aminoglycosides.

ATCC Accession Number

A deposit of Streptomyces YCED 9 was made under the terms of the Budapest Treaty with the American Type Culture Collection (ATCC), Rockville, Md. on Feb. 16, 1995. This strain has been designated ATCC Accession No. 55660.

EXAMPLE IV

Preparation of Stock Cultures of Streptomyces WYE 53 and YCED 9

For short-term use, WYE 53 and YCED 9 are incubated on CYD agar or sporulation agar or, for YCED 9, PDA at 25° C. until sporulated and stored at 4° C. until used. For long-term storage of cultures, 10 ml spore suspensions are prepared by suspending spores from a single agar slant or plate in 10 ml of liquid media. This spore suspension is then used to inoculate 250 ml Erlenmeyer flasks containing 100 ml YGM or PDM as appropriate. The flasks are then incubated with shaking at 250 rpm for 32–36 hours at 30° C. to provide a standard inoculum.

Samples from the standard inoculum are also used for making glycerol cultures suitable for long-term storage at −70° C. and for lyophilization. Alternatively, spores from agar plates or slants can be suspended in sterile 30% (w/v) glycerol solution and frozen at −70° C.

EXAMPLE V

In Vitro Antagonism of Fungal Phytopathogens by Streptomyces WYE 53 and Streptomyces YCED 9

The abilities of Streptomyces YCED 9 and WYE 53 to inhibit the growth of a wide range of fungal phytopathogens were measured in terms of colony growth inhibition. The strains were streak-inoculated to one side of the center of agar plates (potato dextrose agar (PDA)). Inoculated plates were incubated at 25° C. for about 8–12 days until the cultures had sporulated. Sporulation was detectable as a mass of grey aerial mycelium and spores by observation with the naked eye and by phase contrast microscopy (×1,000).

A 5-mm-diameter CMA agar disc containing actively growing mycelium of a specific fungal phytopathogen was taken from the leading edge of a fungal culture and aseptically placed in the center of the agar plate containing either WYE 53, YCED 9 or uninoculated (control). The plates were incubated at 25° C. for five days. Measurements of the diameter (mm) of the phytopathogen growth from the plug in the center of the plate were then taken. The results of these bioassays are shown in Table I below. The results indicate that both YCED 9 and WYE 53 are powerful inhibitors of these three fungal phytopathogens.

TABLE I

| | Antifungal Assay | | |
|---|---|---|---|
| STRAIN | Pythium ultimum | Fusarium oxysporum | Rhizactonia solani |
| Control | 38.1 mm | 27.4 mm | 38.1 mm |
| S. hygroscopicus, strain YCED 9 | 22.7 mm | 16.9 mm | 15.9 mm |
| S. hygroscopicus, strain WYE 53 | 23.5 mm | 16.9 mm | 19.3 mm |

Streptomyces YCED 9 was further tested against a wider range of fungal plant pathogens. YCED 9 was found to exhibit strong antifungal activity against a wide range of fungi including species of Aphanomyces (e.g., A. euteiches), Rhizoctonia, Phytophthora, Fusarium (e.g. F. oxysporum, F. cinnamomi, and F. solani), Pythium (e.g., P. ultimum), Phanerochaete (e.g., P. chrysosporium), and Phytomatotrichum (e.g., P. omnivorum).

EXAMPLE VI

Use of Streptomyces Bacteria and Their Metabolites as a Seed Treatment

Streptomyces YCED 9 and WYE 53 bacteria may be applied to seeds to prevent subsequent fungal infection of seedlings when seeds germinate. Alternatively, seeds may be pretreated with antimicrobial metabolites of YCED 9 or WYE 53 to achieve inhibition of fungal growth. As noted above, YCED 9 produces metabolites that are active against root pathogenic fungi and other pathogenic microorganisms.

Thus, Streptomyces YCED 9 or WYE 53 bacteria can be used to reduce the susceptibility of plants to fungal infection by immersing plant seeds in a composition comprising Streptomyces YCED 9 or WYE 53 and then planting the seeds in a suitable growth medium. The composition containing YCED 9 or WYE 53 in which the seeds are immersed may be formulated as described below for WYE 53 by suspending harvested mycelia or spores of YCED 9 or WYE 53 in a sterilized 3% (w/v) sodium alginate solution to a density of approximately at least $10^4$ cfu/ml. After immersion in this composition, the seeds are planted in a suitable growth medium, such as nursery bedding soil or potting mix. In an alternative embodiment, 1.5% (w/v) methyl cellulose solution may be employed instead of 3% (w/v) sodium alginate solution.

Alternatively, the antimicrobial metabolites (including antifungal metabolites) produced by Streptomyces YCED 9 or WYE 53 may be used to treat the seeds. A composition that contains the antifungal metabolites of YCED 9 or WYE 53 can be produced as described below by growing a bacterial culture of the Streptomyces strain in a suitable growth medium and then harvesting the culture supernatant from this growth medium. These antifungal metabolites may be concentrated by extraction from the culture medium using ether as described below, or used directly. In a preferred embodiment, the antifungal metabolites of YCED 9 or WYE 53 are redissolved in distilled water (or in 6% w/v ethanol), filter sterilized and then added to a 3% (w/v) sodium alginate solution as described above. Seeds are then treated by immersion in this preparation and are then planted in a suitable growth medium.

By way of example, the ability of a third isolate, Streptomyces WYEC 108, to protect plants against phytopathogens was determined by applying strain WYEC 108 to ungerminated chickpea seeds and then planting these seeds in soil infested with the fungal phytopathogens *P. ultimum* and *P. irregulare*. Parallel experiments were performed using extracellular metabolites produced by WYEC 108. Streptomyces WYEC 108 shows similar antifungal activity to Streptomyces WYE 53 and YCED 9. Accordingly, the following experiments are expected to be reliable indicators of the in vivo activities of WYE 53 and YCED 9.

Growth of Streptomyces WYEC 108

For growth of strain WYEC 108 cells, one liter Erlenmeyer flasks containing 500 ml YGM (pH 7.1–7.2) were inoculated with 20 ml of stock culture and incubated with shaking at 250 rpm at 30° C. for 3 days for the production of cell mass. For production of antifungal metabolites, one liter Erlenmeyer flasks containing 500 ml CYD (pH 7.1–7.2) were inoculated with 20 ml of stock culture and incubated with shaking at 250 rpm at 30° C. for 7 days.

Treatment of Seeds with Streptomyces WYEC 108 and Antifungal Metabolites

A mycelial suspension of Streptomyces WYEC 108 was harvested by centrifugation at 5,000 rpm for 10 minutes from a 500 ml 3-day-old YGM liquid culture. The harvested mycelia were resuspended in 200–300 ml of sterilized 3% (w/v) sodium alginate solution to a culture density of $1.0–1.2 \times 10^4$ cfu/ml. Chickpea seeds were then added to the well mixed cell-alginate suspension and the seeds were transferred one by one into sterilized 0.25 M $CaCl_2$ in distilled water. These seeds were used in the biocontrol assay described below.

Antifungal metabolites produced by Streptomyces WYEC 108 were obtained as follows. A 7-day-old 500 ml culture was filtered to remove cells and subsequently extracted with 150 ml ether using an extraction funnel. The ether was then removed by vacuum evaporation and the resulting extracts were redissolved in 1.5 ml distilled water. This solution was then filter sterilized through a sterile 0.45 $\mu$m filter and was added into 10 ml 3% (w/v) sodium alginate solution. The antifungal metabolite-alginate suspension was applied as described above to chickpea seeds for use in the biocontrol assay.

In Vivo Biocontrol Assay

Soil naturally infested with *P. ultimum* and *P. irregulare* is described in "Materials and Methods", above. This agricultural soil was used in this vivo biocontrol assays. Soil pH was determined to be pH 5.6 by thoroughly mixing a soil:water slurry (1:1), allowing the solids to settle for 2 h, and taking the pH of the supernatant solution. The soil was chopped, mixed thoroughly and then placed in seedling pots (10 cm deep×10 cm diameter).

The in vivo biocontrol assay was carried out by planting ungerminated chickpea seeds treated with either Streptomyces WYEC 108 or the antifungal metabolites in the infested soil. Untreated seeds planted in the same soil were used as a control. This procedure involved the following steps:

1) One cm of peat moss was placed in the bottom of each pot to prevent loss of soil while still providing for aeration and drainage.

2) Seedling pots were filled with the infested soil.

3) The soil was then watered to saturation from the bottom. After saturation of the soil surface, untreated and treated chickpea seeds were placed on the soil and covered 1.5–2.0 cm deep with the same soil. The topping was allowed to become wet by capillary action from the column of wet soil beneath. Ten seeds were planted in each of three replicate seedling pots. No fertilizer was added to the soil. To minimize drying and prevent crusting the pots were covered with clean plastic until seedling emergence. Additional water was sprayed on the top of the pots as needed, beginning after seedling emergence. Experiments were performed in a greenhouse at 15–30° C. with a 12 hr light and 12 hr dark cycle photoperiod (16,000 lux).

Emergence counts of chickpea seedlings were made periodically, and final emergence counts were taken after 20 days. Emergence data were reported as the average for each treatment. The ability of Streptomyces WYEC 108 to act as a biocontrol agent was based on total emergence, plant height, and plant fresh weight, as compared to the control plants grown from untreated seeds with the biocontrol agent. The results of this biocontrol assay are shown in Table II.

TABLE II

| Treatment | Dumping-off (%) | | Emergence (%) | Height (cm) | Fresh weight (g/plant) |
| | Preemergence | Postemergence | | | |
|---|---|---|---|---|---|
| Control | 86.7 | 6.6 | 6.7 | $4.3^x$ | $0.34^x$ |
| Streptomyces WYEC 108[c] | 36.7 | 0.0 | 63.3 | 11.3 | 1.05 |
| 3% Alginate[d] | 83.3 | 10.0 | 6.7 | $4.1^x$ | $0.32^x$ |
| Antifungal metabolites[c] | 63.3 | 3.3 | 33.3 | 8.9 | 0.66 |

[c]In 3% alginate, coated on seeds.
[d]Not containing WYEC 108.
[x]Means so marked within column were not significantly different at the P = 0.05 level.

Both Streptomyces WYEC 108 cells and the antifungal metabolites produced by these cells reduced Pythium damping-off of the chickpeas.

Plants showed vigorous growth, when seeds were coated with Streptomyces WYEC 108 cells. There was a significant reduction in height and fresh weight of the plants that emerged from the control (untreated) chickpea seeds as compared to those of the plants germinated from seeds coated with Streptomyces WYEC 108 cells. Emergence of untreated chickpea seeds was extremely reduced (6.7% emergence) because of seed rot and preemergence damping-off disease caused by *P. ultimum* when seeds were planted in soil naturally infested with *P. ultimum* and *P. irregulare*. In contrast, emergence of seeds treated with Streptomyces WYEC 108 cells before seedling was 63.3%. Seeds treated with alginate alone did not show increased emergence. Symptoms typical of Pythium root rot, including root hair loss and root discoloration, were evident in harvested chickpea roots germinated from control seeds, but these symptoms were absent from plants grown from seeds treated with Streptomyces WYEC 108 cells. In the controls, damage to chickpea was mainly in the form of seed decay, and preemergence damping-off. Chickpea seedlings that did emerge and grow were stunted, and their roots were severely infected with *P. ultimum*. In a side by side comparison of chickpea plants taken from the biocontrol assay, the control plant, which was germinated from untreated seeds showed extensive root infection and lack of secondary roots and root hairs whereas the plants emerging from seeds coated with Streptomyces WYEC 108 showed good growth and normal formation of secondary roots and root hairs.

Emergence of chickpea seeds treated with antifungal metabolites in the form of ether soluble metabolite was higher (33.3%) than that of control seeds (6.7%), but lower than that of seeds coated with Streptomyces WYEC 108 cells (63.3%). Plants that emerged from seeds treated with antifungal metabolites showed vigorous growth, longer root, and a higher density of root hair development as compared to control plants.

Accordingly, one aspect of the present invention is the use of Streptomyces YCED 9, WYE 53 or the metabolites of these bacteria in the treatment of seeds.

EXAMPLE VII

Ability of Streptomyces YCED 9 and Streptomyces WYE 53 to Metabolize Turf Thatch An important characteristic of Streptomyces YCED 9 and Streptomyces WYE 53 is their ability to degrade and metabolize lignocellulosic materials, such as turf thatch. Thatch is the dead material including grass stems and other vegetative matter that accumulates in turf. Thatch build up to lawns, golf courses and other cultivated turf grasses can inhibit healthy growth and promote weeds and fungal pathogens, Streptomyces YCED 9 and Streptomyces WYE 53 are able to metabolize turf thatch and utilize it as a carbon source. As a result, these strains are able to effectively colonize and persist in the rhizosphere. The ability of these strains to persist in the rhizosphere enhances their ability to control the growth of fungal pathogens.

The ability of Streptomyces YCED 9 and Streptomyces WYE 53 to metabolize turf thatch is illustrated by experiments in which spores of these strains are incubated with sterile turf thatch. Essentially, 1 g of turf thatch is sterilized by autoclaving for 90 minutes on 3 consecutive days. The sterile flask is then inoculated with spores of the selected Streptomyces strain in a sterile solution of phosphate buffered yeast extract (0.3% w/v, pH 6.5–7.5). Following inoculation, the flask is incubated at 30° C. Replicate flasks are harvested periodically and the amount of thatch remaining is quantified gravimetrically (i.e., the thatch is harvested, washed, dried and weighed). The results of this experiment are shown in Table III below. As shown in this table, up to 20% by weight of the turf thatch is metabolized. This rate of degradation is substantial, considering the highly lignified nature of the turf thatch and its normal recalcitrance to degradation.

TABLE III

| T = weeks | Control grams recovered | Control percent degraded | WYE 53 grams recovered | WYE 53 percent degraded | YCED 9 grams recovered | YCED 9 percent degraded |
| --- | --- | --- | --- | --- | --- | --- |
| 0 | 0.908 g | 0.00% | 0.893 g | 1.65% | 0.891 g | 1.81% |
| 4 | 0.941 g | 0.00% | 0.750 g | 20.30% | 0.800 g | 14.98% |
| 8 | 0.900 g | 0.00% | 0.586 g | 34.89% | 0.599 g | 33.44% |

EXAMPLE VIII

Synergistic Turf Thatch Degradation by the Combination of Streptomyces YCED 9 and Streptomyces WYE 53

The combination of Streptomyces WYE 53 and Streptomyces YCED 9 was found to produce a synergistic result with respect to turf thatch degradation. Experiments performed in the same manner as those described in Example VII are summarized in Table IV below. As shown in this table, although the percentage degradation of turf thatch exhibited by the individual strains after 15 weeks of incubation was 25% (YCED 9) and 22% (WYE 53), the combination of these two strains produced a total degradation of 32% after 15 weeks. It should be noted that the percentage degradation achieved will vary with the age and composition of different turf thatch samples.

TABLE IV

| STRAINS: | Percent Degradation after 15 weeks of incubation | Standard Deviation | Total Weight (grams) | Standard Deviation |
| --- | --- | --- | --- | --- |
| Control (no inoculum) | 0.00 | 0.00 | 0.955 | .01030 |
| YCED 9 | 25.3 | 4.08 | 0.713 | 0.0390 |
| WYE 53 | 22.5 | 6.73 | 0.740 | 0.0643 |
| Combination of YCED 9 and WYE 53 | 32.4 | 1.47 | 0.646 | 0.0014 |

Based on this result, a preferred embodiment of the present invention is a composition useful for the degradation of turf thatch that comprises both Streptomyces YCED 9 and Streptomyces WYE 53 and a delivery medium.

A preferred formulation for the field use of Streptomyces YCED 9 or WYE 53 or a combination of both, is the incorporation of the Streptomyces spores into a delivery medium consisting of peat moss and sand. Preferably, the Streptomyces spores are added to the delivery medium to produce a final concentration of $10^8$–$10^9$ colony forming units per gram of delivery medium. A typical unit of this formulation is produced in the following manner: spores from 50–100 sporulated PDA plates of the selected Streptomyces strain are aseptically scraped off the surface of the plates and added to 90 grams of sterile sand. This sand is then mixed into a mixture of sterile sand/peat moss (in a ratio of 1600 grams of sand to 310 grams of peat moss). This formulation can then be stored at room temperature or in the refrigerators for 6–8 months. Storage for this length of time typically result in less than one log reduction in the viability of the spores. Although the ratio of sand to peat moss may readily be varied, by up to at least 25%, the ratio given above is the preferred ratio.

EXAMPLE IX

Inoculation Density Experiments

Experiments were performed to determine the minimum inoculation concentration required for thatch degradation for YCED 9 and WYE 53. These experiments were set up as described in Example VII. Flasks containing the weighed thatch were inoculated with serial dilutions of the Streptomyces spurs, so as to provide a range of from $10^1$ to $10^5$ colony forming units (cfu) per 1.000 grams of thatch. After 4 and 8 weeks of incubation, three samples from each inoculation density were taken to determine the amount of thatch degradation.

The results, summarized in Table V below, show that approximately 10% thatch degradation can be achieved from any initial inoculum of 100 spores of either YCED 9 or WYE 53 per gram of thatch over an 8 week time period. As little as $10^2$ cfu/g of thatch is thus adequate for biological thatch degradation.

TABLE V

| Strain | cfu per gram thatch | t = 0 weeks | t = 4 weeks | t = 8 weeks | Total Percentage of Degradation |
|---|---|---|---|---|---|
| WYE 53 | 10exp1 | 0.949 | 0.934 (0.0189) | 0.894 (0.0786) | 0.07% |
|  | 10exp2 | 0.962 | 0.886 (0.0462) | 0.807 (0.0415) | 10.3% |
|  | 10exp3 | 0.924 | 0.872 (0.0288) | 0.866 (0.0371) | 3.4% |
|  | 10exp4 | 0.929 | 0.869 (0.0210) | 0.804 (0.0582) | 10.7% |
|  | 10exp5 | n/a | 0.898 (0.0085) | 0.821 (0.900) | 8.8% |
| YCED 9 | 10exp1 | 0.960 | 0.946 (0.0180) | 0.860 (0.0552) | 4.4% |
|  | 10exp2 | 0.950 | 0.877 (0.0488) | 0.813 (0.0105) | 9.7% |
|  | 10exp3 | n/a | 0.893 (0.0518) | 0.762 (0.0720) | 15.3% |
|  | 10exp4 | 1.01 | 0.835 (0.0252) | 0.745 (0.0366) | 17.2% |
|  | 10exp5 | n/a | 0.914 (0.0135) | 0.823 (0.0302) | 8.6% |
| Uninoculated control | 0 | 0.927 | 0.924 (0.0061) | 0.900 (0.638) | 0.0% |

EXAMPLE X

Incorporation of Streptomyces Bacteria into Delivery Medium

A composition suitable for the long term storage of viable Streptomyces spores and suitable for delivery of the spores to plants is formulated as described below.

One liter Erlenmeyer flasks containing 500 ml Potato Dextrose medium (PDM) are inoculated with 20 ml of stock culture (for example Streptomyces YCED 9) and incubated with shaking at 250 rpm at 30° C. for three days. After incubation, the culture is harvested by centrifugation at 5,000 rpm for 10 minutes. The harvested material is resuspended in 1600 ml of 10% PDM and mixed with sterilized 8 g $NH_4Cl$ dissolved in 400 ml distilled water. The two liters of cell and $NH_4Cl$ mixture are then inoculated into a plastic container containing 4 kg sterilized delivery medium consisting of a sand-water-cornmeal mixture in a 9-2-1 (w/w) ratio. The delivery medium is sterilized twice (3 hr at 121° C.) before incubation of the culture. This mixture is incubated for 10–14 days at 25° C. to maximize the number of spores present in the mixture prior to storage at 4° C. until use. The bacteria produce spores during the 10–14 days incubation resulting in increased cfu/g of delivery medium.

Alternatively instead of YGM or PDM media, cells and spores can be produced in CYG medium. As an alternative to harvesting cells by centrifugation, culture flasks may also be allowed to stand so that the bacterial mycelia and spores settle. Thereafter, the clear supernatant is decanted and the concentrated mycelia/spore suspension is inoculated directly into the delivery medium. When this harvesting procedure is utilized, it is not necessary to add $NH_4Cl$ to the medium since the bacterial growth medium is a suitable source of nitrogen.

A preferred formulation for the field use of Streptomyces YCED 9 and WYE 53 is the incorporation of spores into a delivery medium consisting of peat moss and sand. Preferably, the Streptomyces spores are added to the delivery medium to produce a final concentration of $10^8$–$10^9$ colony forming units per gram of delivery medium. A typical unit of this formulation is produced in the following manner: spores from 50–100 sporulated PDA plates of the selected Streptomyces strain are aseptically scraped off the surface of the plates and added to 90 grams of sterile sand. This sand is then mixed into a mixture of sterile sand/peat moss (in a ratio of 1600 grams of sand to 310 grams of peat moss). This formulation can then be stored at room temperature or in the refrigerators for 6–8 months. Storage for this length of time typically result in less than one log reduction in the viability of the spores. Although the ratio of sand to peat moss may readily be varied, by up to at least 25%, the ratio given above is the preferred ratio.

EXAMPLE XI

Protection of Plants Against Fungal Root Pathogens by Streptomyces YCED 9

The ability of Streptomyces YCED 9 to prevent a range of fungal diseases of plants was determined under both laboratory conditions and in field trials. The results of these tests are presented below in Table VI. For these tests, seedlings were treated with Streptomyces YCED 9 and challenged with the fungal pathogen. Results were scored as "+" if treatment with Streptomyces YCED 9 prevented fungal infection of the seedlings based on a visual (naked eye and microscopic) inspection.

TABLE VI

Plants Protected by Strain YCED 9

| Plant | Fungal Pathogen | Diseases | Field Test (+/−) | Lab Test (+/−) |
|---|---|---|---|---|
| Lettuce | Pythium | Damping-off | + | ND |
| Chickpea | Pythium | Seed-rot, root-rot, damping-off | + | ND |
| Green Pea | Pythium, Aphanomyces | Seed-rot, root-rot, damping-off | + | ND |
| Pepper | Phytophthora | root-rot | + | + |
| Cotton | Phytomatotrichum | root-rot | + | + |
| Turf Grass | Fusarium Rhizoctonia | root-rot brown patch | + | + |
| Onion | Phoma | Pink root | + | + |
| Potato | Fusarium Rhizoctonia | wilts, dry-rot canker | + | + |
| Tomato | Fusarium | wilts, crown-rot | + | ND[1] |

[1]Not Done

As shown in Table VI, Streptomyces YCED 9 provides protection against a wide range of fungal diseases in a wide range of plants.

EXAMPLE XII

Production of Spores of Streptomyces Bacteria in Liquid Media

Biocontrol agents must survive for extended periods of time to meet shipping needs and the timing patterns of agricultural uses. The use of spores of strain WYE 53 or strain YCED 9 rather than vegetative cells in particular biocontrol formulations enhances the shelf-life of the biocontrol formulation because the spores retain viability under adverse conditions and over long periods of time.

Typically, spores of Streptomyces species are only produced on solid media. However, as set forth below, the following method was found suitable for producing spores in liquid culture.

Two liter Erlenmeyer flasks containing 1,200 ml medium are each inoculated with 50 ml of stock culture (produced as described in Example II) and incubated with shaking at 250 rpm at 30° C. for 12–18 days. Sporulation broth or potato dextrose medium is a preferred medium. Spore production in the culture is monitored by observing with phase-contrast microscope (×1,000, and stained with methylene blue). Spores are then harvested by centrifugation at 9,000 rpm for 10 minutes.

Thereafter, the spores are resuspended in 1,600 ml of sterilized 10% medium (YGM, sporulation broth or potato dextrose broth as appropriate) and 400 ml of a sterile solution comprising 8 g $NH_4Cl$ in distilled water is added (to produce a final spore density of $1.0-1.2 \times 10^7$ cfu/ml). This spore mixture can be used immediately or stored at 4° C. prior to use.

Spore mixtures produced by the liquid culture method described were tested for viability after four months of storage at 4° C. One ml of spore suspension was inoculated into flasks containing 100 ml of sterilized 10% YGM liquid medium (pH6.5) and incubated with shaking at 250 rpm at 30° C. Germination of spores was observed by phase-contrast microscopy (×1,000, stained with methylene blue). Spores were completely germinated in approximately 8 days. This simple observation test showed no loss in viability after this period of storage.

The spore mixture can then be directly inoculated into a delivery medium, such as 4 kg of a pre-sterilized delivery medium consisting of sand, water and cornmeal in a 9:2:1 (w/w) ratio.

The production of spores directly in liquid culture in the described manner avoids the need for a further incubation of the mixture. The delivery medium containing spores was then stored at 4° C. until used.

The viability of a spore/delivery medium composition formulated as described (sand, water, cornmeal; 9:2:1) was tested for viability as follows. A 1.0 g sample of the delivery medium containing WYEC 108 spores was serially diluted and plated on CYD agar plates. Plates were incubated at 25° C. until colonies were formed. An average level of $10^8$ to $10^9$ cfu/g of delivery medium (dry weight) were recorded with samples stored for 30 days.

Alternatively, the spores from an agar plate of sporulation agar may be resuspended in 10–20 ml of sterile distilled water or YGM broth and mixed into 10–100 grams of delivery medium, to obtain a viable count of $10^{12}$ to $10^{14}$ cfu/g of medium. This mixture is then air-dried, mixed thoroughly and stored at 4° C. until used. This formulation is a concentrated product that can be diluted with additional delivery medium to any desired lower cfu/g final viable count.

EXAMPLE XIII

Stability of Alginate Gel Formulation Containing Streptomyces Bacteria

As described above, one embodiment of this invention is the formulation of Streptomyces YCED 9 or WYE 53 in an alginate gel. This gel mixture is particularly suitable for use in coating seeds. The following experiment was performed to confirm the viability and stability of such alginate preparations.

Mycelia of a selected Streptomyces strain were harvested by centrifugation at 5,000 rpm for 10 minutes from a 500 ml 3-day-old YGM liquid culture. The harvested mycelia were resuspended in 125 ml of 10% YGM and added 125 ml of sterilized 5% (w/v) sodium alginate solution to a culture density of $1.0-1.2 \times 10^4$ cfu/ml. Alginate pellets containing mycelia of the Streptomyces strain were formed by adding cell-alginate suspension drop by drop into sterilized 0.25 M $CaCl_2$ in distilled water.

To determine the viability of the alginate pellets formed by this method, alginate pellets containing the culture were subsequently spread on a sterilized plastic petri dish (10 cm×10 cm) and dried for one hour in a laminar flow sterile air hood. The pelletized Streptomyces sporulated readily following storage at 25° C. for 6 to 8 months (to an average level of $10^8$ to $10^9$ cfu/g dried alginate beads). These spores were readily germinated when they were incubated in sterilized water at 25° C. Germination of the spores were observed by phase-contrast microscopy (×1,000 magnification, stained with methylene blue).

EXAMPLE XIV

Formulation of Delivery Medium Including Streptomyces Bacteria

Having set forth above the characteristics of WYE 53 and YCED 9 and provided methods for producing these biocontrol agents in mycelial form and as spores, and suitable delivery media, it will be apparent to one skilled in the art that the present invention can be modified in a number of ways without departing from the spirit of the invention.

Set forth below are examples of alternative embodiments of the present inventions, together with descriptions of particularly preferred embodiments.

Optimum Culture Conditions

Optimal conditions for growth of strains WYE 53 and YCED 9 include temperatures between 20° C. and 30° C., at pHs between 5.5 and 7.5, and at fermenter agitation speeds between 200 rpm and 300 rpm. The Streptomyces bacteria typically achieve maximal cell mass yields of about 5.3 dry weight grams of biomass/liter in YGM liquid medium with culture conditions of 30° C., pH 6.5, and shaking at 200 rpm for 72 hr (to the end of log phase). Doubling time during logarithmic growth phase is approximately 10 hours. The 72 hr incubation time may be significantly reduced by using higher inoculum levels of log phase cells.

Alternatively, spores may be produced on solid agar media such as sporulation agar. These spores may be directly harvested by scraping into water or a suitable liquid medium such as 10% YGM or 10% potato dextrose medium and then directly introduced into the delivery medium. Alternatively, the spores may be mixed directly into a dry delivery medium such as peat moss/sand. This approach avoids the need for liquid growth of the culture and thereby shortens the production process, while minimizing the possibility of contamination with undesirable microorganisms.

Preferred and Alternative Delivery Media

Streptomyces WYE 53 or Streptomyces YCED 9 may be incorporated into a delivery medium for use in horticultural and agricultural settings. Example X describes one formulation of the delivery medium which comprises sand-water-cornmeal in a 9-2-1 (w/w) ratio. It will be understood by one skilled in the art that the formulation of the delivery medium will be dictated by the particular application for which the biocontrol agent is intended. For example, various organic and inorganic fillers such as clay, vermiculite, wheat bran, corn cobs or chitin can be used as or added to the delivery medium. The ratio of components of a delivery medium will be determined on the basis of texture and physical properties required. For example, properties such as moisture holding ability, light weight for easy handling and transportation, porosity to provide space for mycelial and plant root growth and spread may be important. Alternatively, vegetative mycelia or spores of Streptomyces WYE 53 or Streptomyces YCED 9 can be added to an alginate suspension or a methyl cellulose suspension to produce alginate or methyl cellulose entrapped pellets of these bacteria. Methods of producing alginate pellets are known in the art and are described further in U.S. Pat. No. 4,668,512 to Lewis et al. Other ingredients, such as fertilizers, may also be incorporated into these pellets. These pellets may be particularly useful for broadcast spreading of YCED 9 onto turf (for example, golf courses) to prevent thatch build up and control fungal pathogens.

In a preferred embodiment, the present inventors have determined that a delivery medium comprising peat moss-sand-cornmeal in a 1:3.5:1 weight/weight ratio is particularly suitable. This ratio provides an appropriate density and water holding capacity for the use of this product in agricultural and horticultural applications. However, as stated above, other ratios of these components and of other components are also acceptable as delivery media. For example, an effective alternative delivery medium comprises peat moss (620 g)-sand (3380 g)-cornmeal (270 g)-chitin (10 g). Another delivery medium that is preferred for Streptomyces YCED 9 is sand-peat moss mixed together in a ratio of 1600 grams sand and 310 grams peat moss. The use of this delivery medium is described in Example X.

In one embodiment, approximately 1.6 liters of harvested culture broth (log-phase cells: e.g., about 72 hr culture) containing Streptomyces WYE 53 mycelium or Streptomyces YCED 9 mycelium grown in potato dextrose broth as described above is supplemented with 400 ml of a sterile solution of $NH_4Cl$ (containing 8 g of $NH_4Cl$ in 400 ml distilled water) and inoculated into plastic containers containing 4 kg sterilized Delivery Medium consisting of peat moss, sand, and cornmeal. The Delivery Medium is sterilized twice (3 hours at 121° C.) before inoculation with the bacteria. Inoculated containers are incubated at 30° C. for 10 to 14 days to maximize spore formation. Containers are then stored at 4° C. until used.

The use of $NH_4Cl$ in the delivery medium provides a nitrogen source for the germinating spores of the bacteria. It will be apparent to one skilled in the art that other nitrogen sources besides $NH_4Cl$ can be used for this purpose. For example, and as described herein, when spores are resuspended in bacterial growth medium (such as 10% YGM) prior to incorporation in the delivery medium, the addition of this nitrogen source is unnecessary. In preferred embodiments of the present invention, the delivery medium comprises a sufficient amount of a nitrogen source. It will be apparent to one skilled in the art that the determination of what comprises "a sufficient amount" of a nitrogen source can be made by determining the effects on germination frequency of increasing or decreasing the amount of a particular nitrogen source or the effects of changing the nitrogen source. A sufficient amount of a nitrogen source is that amount of a particular nitrogen source which facilitates germination of the spores.

In an alternative embodiment, as described in Example XII, spores of WYEC 108 or YCED 9 are produced in liquid medium and directly incorporated into the preferred delivery medium which is then stored at 4° C.

In a preferred embodiment of the present invention, Streptomyces bacteria are added to the delivery medium to a final concentration of at least $1 \times 10^5$ cfu/g. In more preferred embodiments, the final concentration of Streptomyces WYEC 108 or Streptomyces YCED 9 in the delivery medium is at least $1 \times 10^8$ cfu/g.

As discussed, one embodiment of the present invention is a composition comprising a biologically pure culture of strain WYE 53 or YCED 9 and a delivery medium. It will be apparent to one skilled in the art that such a composition may be supplemented with additional materials or other microorganisms. For example, fertilizers or chemical pesticides may be added to the composition. In addition, other biological control agents may be combined with the composition. For example, the composition may include both Streptomyces WYE 53 and YCED 9. Other strains of beneficial Streptomyces bacteria may also be combined with either Streptomyces WYE 53 or Streptomyces YCED 9, provided that the additional strains are compatible with WYE 53 or YCED 9. Compatibility can be readily determined by streaking two strains next to each other on an agar plate. If both strains grow, they are compatible. In compatibility is evidenced by the failure of one strain to grow in the presence of the other.

EXAMPLE XIV

Example of Formulation of Delivery Medium Including Streptomyces WYE 53 or Streptomyces YCED 9

A preferred formulation of the delivery medium containing Streptomyces WYE 53 or Streptomyces YCED 9 is produced on a large scale by the procedure set forth below. All of the procedures described are performed using standard aseptic technique (e.g., in a UV light-sterilized laminar flow chamber) to assure asepsis until the packaged bags are opened by final users.

Production of Cells

1) Suspend the spores from a CYD slant of Streptomyces WYE 53 or Streptomyces YCED 9 in 10 ml of sterile sporulation broth or potato dextrose broth. This inoculum suspension is used to inoculate the flask cultures.

2) Inoculate six 250 ml flasks containing 100 ml liquid broth (e.g., YGM, PDB or SB). Use 10 ml of spore suspension per flask as inoculum. After inoculation, flasks are incubated with shaking at 200 rpm and at 30° C. for about 36 hrs.

3) Inoculate six 2.0 liter flasks each containing 1.1 liter of broth (pH 6.5) (YGM, PDB or SB) with the mycelial inoculum prepared above (100 ml of inoculum per flask). After inoculation, flasks are incubated with shaking at 200 rpm and at 30° C. for about 24 to 48 hrs or longer (up to 4 days). This becomes the inoculum for the fermenter.

Fermentation

Approximately 7.2 liter of the stock culture prepared above is inoculated into a fermenter containing 40 liter of sterile broth (pH 6.5 (TGM, PDB or SB) (approximately 15% inoculum by volume; the approach is to inoculate with as high a density of cell suspension as practical). The fermenter is operated with agitation (200 rpm) at 30° C. for about 72 hours (to near the end of log phase).

Fermenter Harvest

1) The fermentation culture broth containing the bacterial cells (after about 72 hrs incubation) is aseptically harvested in sterile 20 liter plastic bottles.

2) Sterile $NH_4Cl$ solution is added to the harvested culture broth, which still contains the bacterial cells (Use 16 g $NH_4Cl$ or YCED9-$NH_4Cl$ dissolved in 800 ml distilled water per 3.2 liter of harvested culture broth; pre-sterilized by autoclaving). The resulting 1.2 liter volume of $NH_4Cl$-containing cell suspension is then mixed well by shaking the bottle before it is inoculated into the previously prepared delivery medium.

Preparation of the Delivery Medium

1) Each component of the Delivery Medium is measured separately and added into a large size sterilizable pan or other suitable container. The combined mixture is defined as the delivery medium. It consists of peat moss, sand, and cornmeal (540 g:2700 g:540 g; 1:3.5:1 w/w ratio). An alternative preferred formulation is sand and peat moss in a 1600 g:310 g ratio.

2) The delivery medium is thoroughly mixed and covered with sturdy aluminum foil or cotton batting and then sterilized twice (90 minutes at a time at 121° C. with 12 hours between sterilization periods).

3) The delivery medium is cooled to room temperature after the second sterilization and before inoculation of the harvested culture broth containing the Streptomyces strain and NH$_4$Cl solution (prepared above).

Incorporation of Streptomyces WYE 53 or Streptomyces YCED 9 into the Delivery Medium to Create a Formulation of Peat Moss, Sand, Water, Cornmeal, and NH$_4$Cl 1) About 0.5 liters of the strain WYE 53-NH$_4$Cl or YCED9-NH$_4$Cl solution (prepared above) is thoroughly incorporated into each of as many as needed presterilized plastic containers containing of 3.78 kg of delivery medium.

2) The inoculated containers are then incubated at 30° C. for 10–14 days (up to 20 days incubation may be optimal) after which they can be stored at 4° C. until used (the formulation is stable for months).

EXAMPLE XV

Incorporation of the Formulation Containing Streptomyces Bacteria into Seedling Nursery Beds The formulation containing the Streptomyces WYE 53 or Streptomyces YCED 9 biocontrol agent and delivery medium as described in Example XIV is mixed with a plant growth medium such as nursery bedding soil or potting mix to a final Streptomyces concentration of $\geq 1.0$–$1.2 \times 10^5$ or more cfu/g-soil). The seedling procedure is as follows.

1) About 1.0 cm of peat moss is placed in the bottom of each pot (or bed) to prevent loss of soil (or potting mix) while still providing for aeration and drainage.

2) Seedling pots are then filled with the agricultural (nursery or potting mix) soil up to about 3.0 cm below from the top of the pots (or beds). The pots (beds) are then watered to saturation.

3) About 1.5 cm of the formulation containing Streptomyces WYEC 108 or Streptomyces YCED 9 and delivery medium is then added to the top of each pot (bed). If desired, the formulation can also pre-mixed with nursery bedding soil or potting soil to increase the volume and adjust the cfu/g count. However, for optimum efficacy, the cfu/g should be maintained at least $10^5$ cfu/g in the final mix.

4) Seeds are placed on the surface of the prepared seedling pots or beds and then covered with an additional 1.5 cm (approximate) of nursery bedding soil or potting soil/mix.

5) A small amount of water is then added to wet the soil and seeds.

6) To minimize drying and to prevent crusting, the pots are typically covered with clean black plastic until seedling emergence (This may not necessary if moisture is controlled).

7) Additional water is sprayed on the top of the pots (or beds) as needed after seedling emergence.

Having provided examples of embodiments of this invention and preferred embodiments, it will be apparent to those skilled in the art that changes and modifications may be made without departing from the present invention and its broader aspects. We therefore intend the appended claims to cover all such changes and modifications falling within the true spirit and scope of the present invention.

REFERENCES

ATCC Catalogue of Bacteria and Bacteriophages, 17th Edition, 1989. American Type Culture Collection, Rockville, Md.

Filnow, A. B. and J. L. Lockwood. 1985. Evaluation of several actinomycetes and the fungus *Hypochytrium catenoides* as biocontrol agents of Phytophthora root rot of soybean. Plant Disease 69:1033–1036.

Ingram, D. M. and R. J. Cook. 1990. Pathogenicity of four Pythium species to wheat, barley, peas, and lentils. Plant Pathology 39:110–117.

Kraft, J. M. and D. W. Burke. 1971. *Pythium ultimum* as a pathogen of beans and peas in Washington. Plant Dis. Rep. 55:1056–1060.

Locci, R. 1989. "Streptomycetes and Related Genera," in *Bergey's Manual of Systematic Bacteriology*, Williams and Wilkens, Baltimore, Md. 4:2451–2492.

Lynch, J. M., R. D. Lumsden, P. T. Atkey, and M. A. Ousley. 1992. Prospects for control of Pythium damping-off of lettuce with Trichoderma, Gliocladium, and Enterobacter spp. Biol. Fertil. Soils 12:95–99.

Lynch, J. M., K. L. Wilson, M. A. Ousley, and J. M. Whipps. 1991. Response of lettuce to Trichoderma treatment. Lett. Appl. Microbiol. 12:59–61.

Miller, J. J. E. Liljeroth, G. Henken, and J. A. van Veen. 1990. Fluctuations in the fluorescent pseudomonad and actinomycete populations of rhizosphere and rhizoplane during the growth of spring wheat. Can. J. Microbiol. 36:254–258.

Pridham, T. G. and D. Gottlieb. 1948. The utilization of carbon compounds by some actinomycetales as an aid for species determination. J. Bacteriol. 56:107–114.

Reddi, G. S., and A. S. Rao. 1971. Antagonism of soil actinomycetes to some soil borne plant pathogenic fungi. Indian Phytopathol. 24: 649–657.

Stanghellini, M. E. and J. G. Hancock. 1970. A Quantitative Method for the Isolation of *Pythium ultimum* from Soil. Phytopathology. 60:551–552.

Stasz, T. E., G. E. Harman and G. A. Marx. 1980. Time and site of infection of resistant and susceptible germinating pea seeds by *Pythium ultimum*. Phytopathology. 70:730–733.

Trapero-Casas, A., W. J. Kaiser and D. M. Ingram. 1990. Control of Pythium seed rot and preemergence damping-off of chickpea in the U.S. pacific northwest and Spain. Plant Dis. 74:563–569.

Westerlund, F. V., Jr., R. N. Campbell and K. A. Kimble. 1974. Fungal root rots and wilt of chickpea in California. Phytopathology 64:432–436.

I claim:

1. A biologically pure culture of a microorganism having all of the identifying characteristics of Streptomyces sp. WYE 53 ATCC 55750.

2. A composition comprising cells or spores of Streptomyces sp. WYE 53 ATCC 55750 and a delivery medium.

3. A composition according to claim 2 wherein the composition further comprises a container for containing the Streptomyces sp. WYE 53 ATCC 55750 and delivery medium.

4. A composition produced by:
   (a) growing a biologically pure culture of Streptomyces sp. WYE 53 ATCC 55750;
   (b) harvesting spores or cells from said culture; and
   (c) combining said spores or cells with a delivery medium.

5. A composition according to claim 4 wherein the composition further comprises cells or spores of Streptomyces sp. YCED 9 ATCC 55660.

6. A method for reducing the susceptibility of a plant to fungal infection wherein the method comprises delivering to the roots of the plant a composition according to claim 2.

7. A method for reducing the susceptibility of germinating seeds to fungal infection, comprising immersing plant seeds in a composition comprising cells or spores of Streptomyces sp. WYE 53 ATCC 55750, and planting the seeds in a suitable growth medium under conditions suitable for germination.

8. A method for degrading turf thatch where the method comprises contacting the turf thatch with a composition comprising:
   (a) cells or spores of Streptomyces sp. YCED 9 ATCC 55660 and a delivery medium; or
   (b) cells or spores of Streptomyces sp. WYE 53 ATCC 55750 and a delivery medium; or
   (c) cells or spores of Streptomyces sp. YCED 9 ATCC 55660 and cells or spores of Streptomyces sp. WYE 53 ATCC 55750 and a delivery medium.

* * * * *